United States Patent

Calton et al.

[11] 4,147,798
[45] Apr. 3, 1979

[54] ANTINEOPLASTIC AGENT

[75] Inventors: Gary J. Calton, Elkridge; Marlin A. Espenshade; Richard L. Ranieri, both of Ellicott City, all of Md.

[73] Assignee: W. R. Grace & Co., New York, N.Y.

[21] Appl. No.: 899,616

[22] Filed: Apr. 24, 1978

Related U.S. Application Data

[63] Continuation-in-part of Ser. No. 821,087, Aug. 2, 1977, abandoned.

[51] Int. Cl.² .................. A61K 31/365; C07D 311/94; C12D 13/00
[52] U.S. Cl. .................. 424/279; 260/343.42; 195/81
[58] Field of Search ...................... 260/343.42; 195/81; 424/279

[56] References Cited
PUBLICATIONS
Sakiko Chemical Abstracts, vol. 56, 13352.

Karklins et al., Chemical Abstracts, vol. 83, 1975, 1584472.
Murray et al., Chemical Abstracts, vol. 49, 4076e.
Elnaghy et al., Chemical Abstracts, vol. 85, 1975, 76309h.

Primary Examiner—Natalie Trousof
Assistant Examiner—Jane T. Fan

[57] ABSTRACT

Disclosed herein is a method of culturing *Aspergillus terreus* strain NRRL 11156 to produce an antineoplastic compound designated as quadrone and having the following structure:

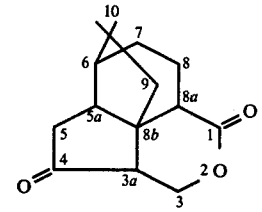

7 Claims, 2 Drawing Figures

ANTINEOPLASTIC AGENT

The invention described in the present application was in part reduced to practice under HEW Contract Number ND1-CM-67074.

CROSS-REFERENCE TO RELATED APPLICATIONS

The present application is a continuation-in-part of an abandoned U.S. patent application Ser. No. 821,087, filed Aug. 2, 1977 by Gary Jim Calton, Marlin Alwine Espenshade and Richard Leo Ranieri, entitled "Novel Antineoplastic Agent".

BACKGROUND OF THE INVENTION

The microorganism *Aspergillus terreus* is known to produce a wide variety of chemical substances depending upon the strain employed and the culture conditions. See *Antibiotics, Origin, Nature and Properties* by Korzybski et al, Pergamon Press, 1967. Specifically, the above reference attributes production of citrinin, flavipin, geodin, erdin, and terreic acid to fermentation activity of *Aspergillus terreus*.

DESCRIPTION OF THE INVENTION

Figure 1:
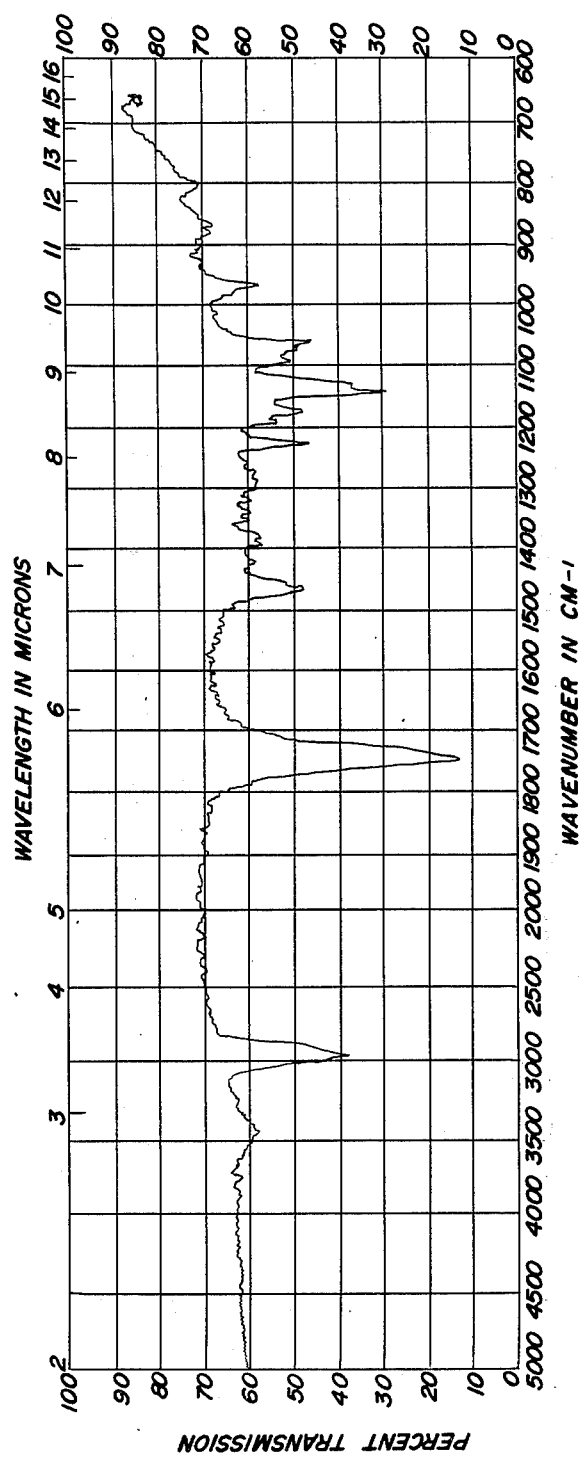
FIG. 1 depicts the IR spectrum of quadrone.

The invention is a process for producing a complex quadracyclic lactone (designated as quadrone) which comprises cultivating the microorganism *Aspergillus terreus* (strain NRRL-11156) under submerged aerobic conditions in an aqueous carbohydrate solution containing a nitrogenous nutrient. The fermentation is carried on until a substantial amount of quadrone is produced, i.e. a yield $\geq 0.001$ mg./ml. of fermentation broth. The yield level is determined by the isolation of quadrone as described in Example 3 below.

The cultivation or fermentation step is generally carried out at from about 22° to 30° C. and for periods of at least 4 days. Preferably, the temperature is 25° C. If the time period is reduced below 4 days, quadrone is still produced but the quantity is reduced. Accordingly, the 4-day period is not critical but is simply a desirable feature to achieve a desirable yield. Preferably a period of 7-15 days is employed. To date optimal results have been obtained after 12 days at an aeration ratio (defined below) of about 0.1. The medium contained in the fermentation broth is not believed to be critical so long as the protein and carbohydrate sources are present. Similarly, it is believed that the concentrations of the minerals (e.g. $FeSO_4.7H_2O$, $K_2HPO_4$) used in the medium can also vary widely. To maximize yield levels it is suggested that the concentrations employed in the examples be maintained. However, the medium can be modified, as would be apparent to one of ordinary skill in the art, by varying the concentration of ingredients. Suitable carbohydrate source materials include molasses, corn syrup, glucose, whey, soluble starches from corn, potatoes, carob beans (and other beans), casava, bananas, and grain. Suitable nitrogenous nutrients include proteins such as meals from soybeans, corn, grains and cottonseed, bran, yeast extracts, meat extracts (beef, pork, fish, chicken), fish meal and dairy products (e.g. casein, skim milk), and their break-down products, e.g. amino acids and other compounds containing nitrogen.

The fermentation is generally carried out under "submerged aerobic conditions". The term "submerged" is used in the sense that the microorganisms are suspended in an aqueous medium during the fermentation. The fermentation conditions are aerobic in the sense that the fermentation broth should be agitated to introduce air. This can be accomplished by simple stirring and/or sparging with air. Examples of suitable stirring rates would be from 100 to 400 rpm. Air can be sparged through the broth at, for example, from 0.025 to about 1 volumes of air per minute per volume of medium, i.e. the aeration ratio is 0.025 to about 1. The rates of stirring and aeration are not critical and are given merely for purposes of illustration. Obviously, the above rates can vary depending upon the size of the sample. Generally, the rate of aeration can be increased to maximize yields.

Quadrone can be isolated from the fermentation broth by extraction with suitable solvents, e.g. n-butanol, chloroform, ethyl acetate, ethyl ether and tetrahydrofuran. Selection of the solvent is not believed to be critical to practice of the invention, and solvents other than those set forth can be employed, especially solvents having polarity similar to those described above.

Following extraction, quadrone is isolated from the solvent extract using customary organic procedures, e.g. the extract can be evaporated to dryness and the quadrone can then be redissolved and crystallized from methanol/water or other solvent systems. Here again, methanol/water has been found to work well but is not believed to be critical in the sense that other solvent systems could likewise be employed, e.g. ethanol/water, methanol, ethanol. chloroform/cyclohexane, cyclohexane or ethyl acetate.

In addition to solvent extraction, quadrone can also be isolated from the fermentation broth using other techniques. For example, the fermentation broth may be passed through a macromolecular resin such as a polystyrene/divinylbenzene resin. An example of such a resin is XAD-2 by Rohm and Haas which has a helium porosity (volume %) of 40; surface area of 300 $m^2/g$. and an average pore diameter of about $90 \times 10^{-8}$ cm. Quadrone will adhere to the surface of the resin and may be subsequently removed by desorption with lower alcohols, e.g. methanol or solutions of methanol/water.

A further method of isolating quadrone involves preparative thin layer chromatography. Quadrone may be visualized by Method 11, (Stahl, 2nd edition, page 857) using the modified spray reagent designated as a light yellow spot with $RF=0.6-0.7$. Subsequently, a solvent extract of quadrone is subjected to chromatography on a silica gel plate as described by Stahl, *Thin Layer Chromatography* (second edition), pages 97-101. Crystals of quadrone are obtained by elution with methanol (or similar solvents) from the silica followed by concentration of the methanol to obtain a saturated solution followed by slow cooling to form crystals. As would be apparent to one of ordinary skill in preparative chemistry, quadrone can be eluted from the silica gel plates with other solvent systems (e.g. ethanol or chloroform), and other methods can be employed to form crystals, e.g. the methanol extract can be stripped and the resulting material redissolved in methanol/water followed by cooling to form crystals.

Quadrone produced as described has been found to inhibit the growth of cancerous human nasopharynx cells. This is a recognized test for antitumor activity, e.g. see *Cancer Chem. Rpts.* 25, 52 (1962). Quadrone is also relatively non-toxic in mice.

Structure of Quadrone

The compound produced as exemplified below was analyzed by IR, NMR, mass spectrometry and UV. The carbon-13 NMR spectrum was also obtained. Based on these analyses and X-ray crystallography the following structure was assigned:

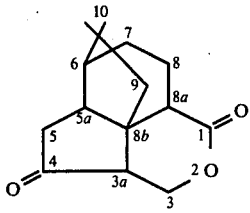

The above compound has been designated as "quadrone". Using recognized ACS nomenclature, the formal name is octahydro-10, 10-dimethyl-6,8b-ethano-8bH-cyclopenta[de][2]-benzopyran-1,4-dione.

Quadrone has a molecular weight of 248.1418 as determined by high resolution mass spectrometry. This corresponds to an empirical formula of $C_{15}H_{20}O_3$ (calculated 248.1412).

The IR spectrum (FIG. 1) shows adsorptions at 1745 $cm^{-1}$ indicating the presence of a 5-membered ketone or a δ-lactone and at 1390 and 1375 $cm^{-1}$ indicating the presence of a geminal dimethyl group. The UV spectrum of quadrone showed a weak absorption at 280 nm.

Figure 2:
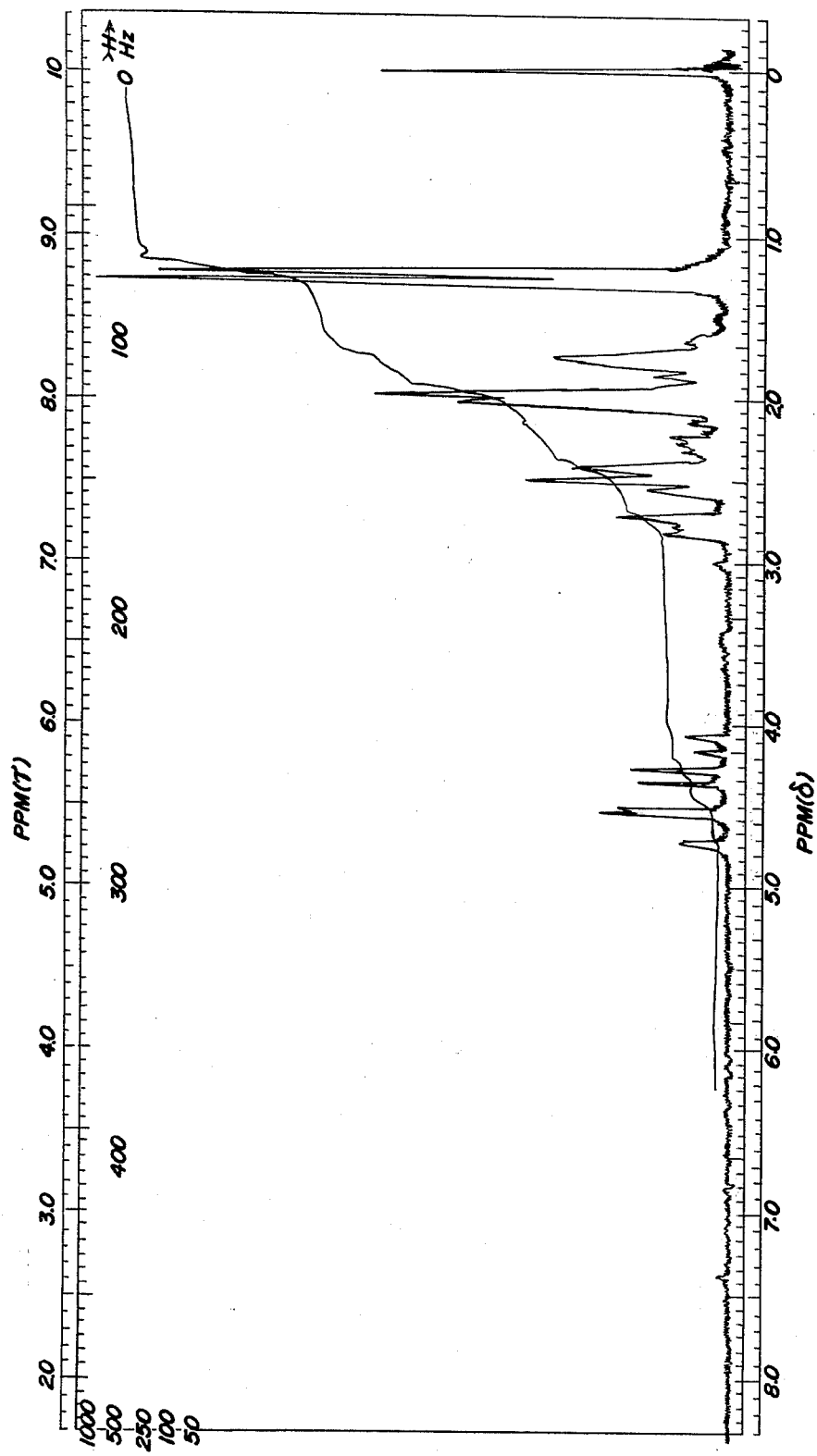
FIG. 2 depicts the proton NMR spectrum of quadrone.

The proton NMR spectrum (FIG. 2) confirmed the presence of a geminal dimethyl group with two, 3 proton singlets at δ1.24 and δ1.28. The two, one proton doublet of doublets centered at 4.23 (J=12, 5Hz) and 4.65 (J=12, 1Hz) are characteristic of non-equivalent methylene protons adjacent to a δ-lactone ring.

Adsorption observed in the carbon-13 NMR spectrum is shown in the following table.

| Carbon-13 NMR Chemical Shifts and Assignment | |
|---|---|
| Chemical Shift | Assignment |
| 19.23 | methylene carbon |
| 26.85 | methyl carbon |
| 28.00 | methylene carbon |
| 34.74 | methyl carbon |
| 40.32 | quaternary carbon |
| 43.17 | methylene carbon |
| 45.80 | methine carbon |
| 48.54 | methine carbon |
| 49.69 | quaternary carbon |
| 52.05 | methine carbon |
| 52.21 | methine carbon |
| 52.38 | methylene carbon |
| 65.20 | methylene carbon adjacent to lactone |
| 174.06 | carbonyl carbon |
| 216.52 | carbonly carbon |

Deposit and Morphology of NRRL 11156

The strain of *Aspergillus terreus* employed to produce quadrone is believed to be novel and has been deposited with ARS Culture Collection Investigations, Northern Utilization Research and Development Division, U.S. Department of Agriculture, Peoria, Illinois 61604 and added to its permanent culture collection as NRRL 11156.

The organism which produces quadrone was obtained from a soil sample from Tipperary, Northern Territory, Australia. The organism has been identified as *Aspergillus terreus* by comparison of the morphology (Table A) and colony characteristics (Table B) with those given by Raper and Fennel.[1]

[1] Raper and Fennel — *The Genus Aspergillus*, Williams and Wilkens, Baltimore, MD, (1965), Chapter 26, pp. 567–577.

Table A— Morphology of the Organism

Conidial head: columnar, 25–50μ×100–175μ in length, uniform in diameter. Very young heads, with 1–5 conidia in a chain, are spherical, but become columnar as they near maturity.

Conidiophores: smooth, 4–5μ×150–200μ.

Vesicles: 7–17μ in diameter and spherical with some showing a slight pyriform contour. C Sterigimata: primary series are 5–6μ×2–3μ with a phialide shape; secondary series are 5–7μ×2μ.

Conidia: globose with a smooth wall and are 2–2.5 μ in diameter.

Table B

| | Colony Characteristics at 25° After Eight Days Growth | | |
|---|---|---|---|
| Medium | Colony Size | Color | Remarks |
| Czapek-Dox | 15 mm | White-Fawn | conidiophores immature |
| Steep Water Agar | 30–35 mm | Buckskin Yellow in Reverse | |
| Potato Dextrose Agar | 25–40 mm | Fawn-Buckskin | |
| Sabouraud's Dextrose Agar | 50–60 mm | Fawn | |
| Malt Yeast Agar | 40 mm | Fawn | |

Example 1—Production of Quadrone 16×

A lyophilized sample of *Aspergillus terreus* (NRRL No. 11156) was dissolved in 2 ml. of 2% malt extract solution. The resulting suspension was smeared over the surface of a 16×125 mm. potato dextrose agar slant which was incubated at 30° C. for 7 days. The resulting culture was suspended in 10 ml. of water to yield a suspension containing approximately $10^6$–$10^{10}$ spores/ml.

Twenty ml. of suspension prepared as above was used to inoculate 1 liter of medium contained in a 4-liter stir jar. The medium had the following composition:

| Medium Composition | | |
|---|---|---|
| Glucose | 40 | g./l. |
| Cottonseed meal | 3 | g./l. |
| Corn germ meal | 1 | g./l. |
| Soybean oil meal | 1 | g./l. |
| $K_2HPO_4$ | 1 | g./l. |
| $MgSO_4 \cdot 7H_2O$ | 1 | g./l. |

-continued

| Medium Composition | | |
|---|---|---|
| FeSO$_4$ . 7H$_2$O | 0.01 | g./l. |
| CaCO$_3$ | 10 | g./l. |
| NaCl | 0.5 | g./l. |

Sufficient deionized water was added to the above medium to produce 1 liter of broth. Following inoculation, the broth was incubated at 25° C. for 3 days with continuous stirring at 250 rpm. Two liters of the broth were used to inoculate 20 liters of broth as above with the exception that no corn germ or soybean oil meal was employed and FeSo$_4$.7H$_2$O was decreased 0.001 g./l., i.e. the only nitrogen source was cottonseed meal. The pH of the broth was adjusted to 6.9-7.1 and was incubated at 25° C. for 7 days. The final pH was 6.0-6.5. The broth also contained 0.5-2% by weight of glucose.

During both of the incubation steps a sufficient amount of Pluronic PL-61 (an oxyethylene/oxypropylene block copolymer by BASF-Wyandotte) was employed to minimize foaming. Generally, the amount of surfactant was about 0.15%. During the second incubation step the broth was stirred continually at 350 rpm. Also, air was sparged through the broth at approximately 2 liters/minute.

Example 2—Isolation of Quadrone

Twenty liters of broth produced as described was filtered to remove the mycelial mass (about 1 liter). The filtrate was contacted with 4 equal portions of n-butanol in a 4/1,v/v ratio. The quadrone, being soluble in the n-butanol, was thereby separated and following combination, the n-butanol extracts are evaporated to dryness over a water bath at 40° C. (~1 mm./Hg.) using a thin film rotary evaporator. The resulting gum was triturated with about 0.5 liters of chloroform which was stripped as above to yield a thick brown oil. The oil was dissolved in methanol/water from which quadrone crystallized by seeding. Using the above procedure, the yield of quadrone is generally 0.2 mg./ml. of the original fermentation broth. To maximize purity, further recrystallizations can be accomplished using methanol/water. In situations where this has been done, the yield is generally still above 0.1 mg./ml.

Example 3—Isolation of Quadrone by Preparative Thin Layer Chromatography

The brown oil produced in Example 2 above has also been processed by streaking across a 20×20 mm. silica gel plate (1 mm. thickness). The fluid in the developing tank was 9:1 chloroform/methanol. Development was carried out at room temperature. Visualization (Stahl, 2nd edition, page 857, Method 11) was carried out using p-anisaldehyde, sulfuric acid, acetic acid and ethanol (0.5:0.5:0.1:9) spray by heating at 110° F. until maximum color development occurred. Quadrone develops a light yellow spot. Subsequently (using other plates), the quadrone was isolated according to the method described in Stahl, 2nd edition, (pages 97-101).

Quadrone is generally separated from the silica gel plates by suspending the scrapings in methanol, filtering, stripping to dryness, followed by crystallization from methanol/water. Recrystallization from methanol/water is generally carried out at least one time. Yields using thin layer chromatography are generally at least 0.01 mg./ml.

Example 4—Quadrone Toxicity

Crystals of quadrone were suspended in carboxymethylcellulose (10 mg. in 1 ml. of CMC) and injected into mice at various levels. Doses as high as 340 mg./kg. of body weight did not exhibit a lethal effect.

Example 5—Activity Against Tumor Cells

Tumorous human nasopharynx cells (also known as KB cells) were obtained. Following the procedure set forth in *Cancer Chem. Rpts.* 25, 52 (1962), the KB cells were cultured and inoculated with various levels of quadrone. It was established that the ED50 was 1.3 µg./ml. Using the prescribed test procedure, levels of 4 µg./ml. or less indicate activity against tumor cells.

Example 6 the anti-tumor activities of quadrone were tested in mice (BDF strain, female, 18-22 g., 10-membered group for each dosage level as well as a similar 10-membered group to constitute the control) with Lewis Lung Carcinoma. The following table describes the dosage levels and results of the tests. The quadrone was dissolved in dimethyl sulfoxide as the carrier and the resulting solution was administered into the abdominal cavity once daily, starting on the day following the day of implantation of the tumor. In the test population the dosage level was administered once daily for 9 days. At dosage levels above 3.0 mg./kg. the quadrone preparation was found to be active.

TABLE C

| Dosage Level | Cures | Tumor Evaluation | | Life Extension (%) |
|---|---|---|---|---|
| | | Test | Control | |
| 96.0 | 2 | 31.0 | 21.0 | 147 |
| 48.0 | 3 | 38.0 | 21.0 | 180 |
| 24.0 | 2 | 39.0 | 21.0 | 185 |
| 12.0 | 5 | 60.0 | 21.0 | 285 |
| 6.0 | 4 | 34.0 | 21.0 | 161 |
| 3.0 | 2 | 28.0 | 21.0 | 133 |
| 1.50 | 2 | 23.0 | 21.0 | 109 |

From the above table is can be seen that ½ of the animals in each control group had died by the end of 21 days following implantation of the tumor. The greatest activity for the quadrone preparation appeared at a dosage level of 12 mg. per kg. In this test ½ of the test group of 10 animals was alive after 60 days indicating a "life extension" of 285% (60/21 times 100). Similarly, the other levels of administration gave life extensions ranging from 109 to 185%. For purposes of the test, each animal was considered "cured" if it was alive at the end of 60 days and exhibited no evidence of the tumor being present. It can be seen that the dosage level of 12 mg./kg. provided a cure for 5 of the 10 treated animals.

What is claimed is:

1. The process of producing a complex quadracyclic lactone designated as quadrone, which comprises cultivating the microorganism *Aspergillus terreus* NRRL 11156 under submerged aerobic conditions in an aqueous carbohydrate solution containing a nitrogenous nutrient until a substantial amount of quadrone is produced.

2. A method as in claim 1 wherein the microorganism is cultured at a temperature of from about 22° to about 30° C. for from about 4 to 15 days.

3. A method as in claim 1 including the additional step of recovering quadrone from the fermentation broth.

4. A method as in claim 1 wherein the microorganism is cultured at about 25° C.

5. A method as in claim 1 wherein the microorganism is cultured until the level of quadrone in the fermentation broth is at least 0.001 mg./ml.

6. Octahydro-10, 10-dimethyl-6,8b-ethano-8bH-cyclopenta[de][2]benzopyran-1,4-dione corresponding to the structural formula:

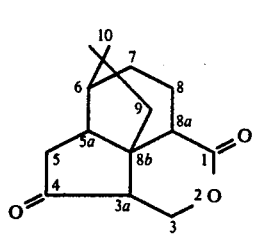

7. A method of inhibiting the growth of tumorous human nasopharynx cells in mice comprising inoculating said cells with an effective amount of octahydro-10, 10dimethyl-6,8b-ethano-8bH-cyclopenta[de][2]benzopyran-1,4-dione.

* * * * *